(12) United States Patent
Asano et al.

(10) Patent No.: US 11,229,718 B2
(45) Date of Patent: Jan. 25, 2022

(54) AIR CLEANING APPARATUS

(71) Applicant: NIKKISO CO., LTD., Tokyo (JP)

(72) Inventors: Hideki Asano, Tokyo (JP); Koichi Sugimoto, Tokyo (JP)

(73) Assignee: NIKKISO CO., LTD., Tokyo (JP)

( * ) Notice: Subject to any disclaimer, the term of this patent is extended or adjusted under 35 U.S.C. 154(b) by 119 days.

(21) Appl. No.: 16/492,028

(22) PCT Filed: Nov. 24, 2017

(86) PCT No.: PCT/JP2017/042165
§ 371 (c)(1),
(2) Date: Sep. 6, 2019

(87) PCT Pub. No.: WO2018/163526
PCT Pub. Date: Sep. 13, 2018

(65) Prior Publication Data
US 2020/0268927 A1 Aug. 27, 2020

(30) Foreign Application Priority Data
Mar. 8, 2017 (JP) .............................. JP2017-044275

(51) Int. Cl.
*A61L 9/20* (2006.01)
*F24F 8/10* (2021.01)
(Continued)

(52) U.S. Cl.
CPC ............ *A61L 9/205* (2013.01); *B01D 53/885* (2013.01); *B01J 21/063* (2013.01); *B01J 27/16* (2013.01);
(Continued)

(58) Field of Classification Search
CPC ........... A61L 9/205; F24F 8/10; B01D 53/885
See application file for complete search history.

(56) References Cited

U.S. PATENT DOCUMENTS 5,919,422 A * 7/1999 Yamanaka ............. B01J 35/004
422/121
2002/0037240 A1 3/2002 Okada et al.
(Continued)

FOREIGN PATENT DOCUMENTS

CN 204648461 U 9/2015
JP 2000005629 A * 1/2000
(Continued)

OTHER PUBLICATIONS

English Translation of Japanese Document No. JP2005342509A provided by the European Patent Office website espacenet.com: Miyagawa; Air Sterilizer/Deodorizer; Dec. 15, 2005 (Year: 2005).*

*Primary Examiner* — Kevin Joyner
(74) *Attorney, Agent, or Firm* — Muncy, Geissler, Olds and Lowe, P.C.

(57) ABSTRACT

An air cleaning apparatus includes: a collection filter for collecting dust; a first ultraviolet light emitter for irradiating the collection filter with ultraviolet light having a first wavelength; and a photocatalyst supporting filter which supports a photocatalyst exhibiting photocatalytic activity by the ultraviolet light having the first wavelength and collects the dust. The collection filter transmits the ultraviolet light having the first wavelength, and the ultraviolet light having the first wavelength passing through the collection filter is irradiated to the photocatalyst supporting filter.

7 Claims, 1 Drawing Sheet

(51) Int. Cl.

| | | |
|---|---|---|
| *B01D 53/88* | (2006.01) | |
| *B01J 21/06* | (2006.01) | |
| *B01J 27/16* | (2006.01) | |
| *B01J 35/00* | (2006.01) | |
| *B03C 3/155* | (2006.01) | |
| *F24F 1/00* | (2019.01) | |
| *F24F 8/24* | (2021.01) | |

(52) U.S. Cl.
CPC .............. *B01J 35/004* (2013.01); *B03C 3/155* (2013.01); *F24F 1/00* (2013.01); *F24F 8/10* (2021.01); *A61L 2209/12* (2013.01); *A61L 2209/14* (2013.01); *B01D 2255/802* (2013.01); *B01D 2257/91* (2013.01); *F24F 8/24* (2021.01)

(56) References Cited

U.S. PATENT DOCUMENTS

| | | | |
|---|---|---|---|
| 2005/0215430 | A1 | 9/2005 | Tamai |
| 2015/0174528 | A1* | 6/2015 | Son .................... B01D 53/885 422/169 |

FOREIGN PATENT DOCUMENTS

| | | | |
|---|---|---|---|
| JP | 2004-060947 | A | 2/2004 |
| JP | 2005-342509 | A | 12/2005 |
| JP | 2010-284431 | A | 12/2010 |
| JP | 2011-056155 | A | 3/2011 |
| KR | 10-2003-0088745 | A | 11/2003 |
| KR | 10-0770149 | B1 | 10/2007 |
| KR | 10-2009-0122756 | A | 12/2009 |

* cited by examiner

AIR CLEANING APPARATUS

TECHNICAL FIELD

The present invention relates to an air cleaning apparatus, and particularly to the apparatus suitable for inactivating bacteria and viruses.

BACKGROUND ART

In the air cleaning apparatus using a filter, the bacteria and viruses tend to be collected on the filter together with dust. The bacteria and viruses are preferably inactivated. It is known to use ultraviolet light to inactivate such bacteria and viruses.

Such an air cleaning apparatus is described in Patent Literature 1 below. The air cleaning apparatus includes several filters, an ultraviolet light emitter, and a photocatalyst supporting layer irradiated with ultraviolet light from the ultraviolet light emitter. The bacteria and viruses collected in the photocatalyst supporting layer are inactivated by a photocatalyst exhibiting photocatalytic activity by the ultraviolet light.

CITATION LIST

Patent Literature

[Patent Literature 1] JP2005-342509 A

SUMMARY OF INVENTION

The photocatalyst supporting layer described in Patent Literature 1 can be said to be a photocatalyst supporting filter for collecting the bacteria and viruses. As described above, the bacteria and viruses collected on the photocatalyst supporting filter are inactivated by irradiation of ultraviolet light, however, the bacteria and viruses are also collected on filters other than the photocatalyst supporting filter. There is a demand for inactivation of the bacteria and viruses collected on collection filters other than such a photocatalyst supporting filter by the ultraviolet light. In this case, it is preferred that the ultraviolet light emitted from the ultraviolet light emitter be used efficiently.

Therefore, an object of the present invention is to provide the air cleaning apparatus capable of inactivating the bacteria and viruses collected on the collection filters and the photocatalyst supporting filter using the ultraviolet light, and efficiently using the ultraviolet light.

In order to solve such problems, the air cleaning apparatus of the present invention includes: a collection filter that collects dust; a first ultraviolet light emitter that irradiates the collection filter with ultraviolet light having a first wavelength; and a photocatalyst supporting filter that supports a photocatalyst exhibiting photocatalytic activity by the ultraviolet light having the first wavelength and collects the dust. The collection filter transmits the ultraviolet light having the first wavelength, and the ultraviolet light having the first wavelength passing through the collection filter is irradiated to the photocatalyst supporting filter.

According to such an air cleaning apparatus, the dust can be collected on the photocatalyst supporting filter and the collection filter. Even when the bacteria and viruses are attached to the collected dust or when the bacteria and viruses are directly collected, since the collection filter and the photocatalyst supporting filter are irradiated with the ultraviolet light from the first ultraviolet light emitter, the bacteria and viruses can be inactivated. Further, the ultraviolet light irradiated to the photocatalyst supporting filter is the ultraviolet light passing through the collection filter. Therefore, according to the air cleaning apparatus of the present invention, it is possible to efficiently use the ultraviolet light emitted from the first ultraviolet light emitter.

Further, the collection filter is preferably made of a light transmitting material.

Since the collection filter is made of the light transmitting material, the ultraviolet light can pass through the collection filter also from other than micropores of the collection filter. Therefore, the ultraviolet light can more easily pass through the collection filter, and the ultraviolet light can be more efficiently irradiated to the photocatalyst supporting filter.

When the collection filter is made of the light transmitting material as described above, the collection filter is preferably made of a nonwoven fabric.

Since the collection filter is made of a light transmitting nonwoven fabric, the ultraviolet light can be scattered by the collection filter. Therefore, even if transmission of the ultraviolet light irradiated to a portion of the collection filter to which the dust adheres is suppressed by the dust, the ultraviolet light irradiated to the other portion of the collection filter is scattered during transmission, which makes it possible to narrow a portion difficult to be irradiated with the ultraviolet light of the photocatalyst supporting filter.

Further, when the collection filter is made of the light transmitting material as described above, the collection filter and the photocatalyst supporting filter are preferably stacked in contact with each other.

In a portion where the collection filter and the photocatalyst supporting filter are in contact with each other, the ultraviolet light is more easily propagated from the collection filter to the photocatalyst supporting filter than in a portion where the collection filter and the photocatalyst supporting filter are separated from each other. Therefore, when the collection filter and the photocatalyst supporting filter are stacked in contact with each other as described above, the ultraviolet light can be efficiently irradiated to the photocatalyst supporting filter from the collection filter as compared to when the collection filter and the photocatalyst supporting filter are separated from each other.

Further, the collection filter is preferably positively charged.

Generally, the dust, bacteria and viruses are negatively charged. Therefore, by the collection filter being positively charged, the dust, bacteria and viruses can be more efficiently collected on the collection filter. Further, when a member is irradiated with ultraviolet light, electrons of atoms or molecules constituting the member tend to be released by the ultraviolet light. Therefore, even if positive charge of the collection filter is reduced by receiving the electrons from the negatively charged dust, bacteria, viruses and the like, the positive charge of the collection filter can be sustained for a longer period of time by irradiation of the ultraviolet light to the collection filter.

Further, in the above air cleaning apparatus, it is preferable to further include a second ultraviolet light emitter that irradiates ultraviolet light having a second wavelength different from the first wavelength to a side opposite to a side of the photocatalyst supporting filter irradiated with the ultraviolet light having the first wavelength. It is preferred that the photocatalyst supporting filter supports the photocatalyst exhibiting photocatalytic activity by the ultraviolet light having the first wavelength on the side irradiated with the ultraviolet light having the first wavelength, and supports the photocatalyst exhibiting photocatalytic activity by irradiation of the ultraviolet light having the second wavelength on the side irradiated with the ultraviolet light having the second wavelength.

According to such an air cleaning apparatus, it is possible to irradiate the ultraviolet light from both sides of the photocatalyst supporting filter. Therefore, the photocatalyst can exhibit high photocatalytic activity on both a side irradiated with the ultraviolet light having the first wavelength and a side irradiated with the ultraviolet light having the second wavelength of the photocatalyst supporting filter. In addition, since the pieces of ultraviolet light of different wavelengths are irradiated to the photocatalyst supporting filter, it is possible to individually select a combination of the ultraviolet light having the first wavelength and the photocatalyst supported on the side irradiated with the ultraviolet light having the first wavelength, and a combination of the ultraviolet light having the second wavelength and the photocatalyst supported on the side irradiated with the ultraviolet light having the second wavelength. Therefore, a degree of freedom in design can be improved. Note that the photocatalyst supported on the side irradiated with the ultraviolet light having the first wavelength of the photocatalyst supporting filter and the photocatalyst supported on the side irradiated with the ultraviolet light having the second wavelength of the photocatalyst supporting filter may be the same photocatalyst. In this case, the photocatalyst exhibits photocatalytic activity by either the ultraviolet light having the first wavelength or the ultraviolet light having the second wavelength.

Further, the photocatalyst supported on the side irradiated with the ultraviolet light having the second wavelength may exhibit photocatalytic activity also by irradiation of the ultraviolet light having the first wavelength, and the ultraviolet light having the first wavelength may also be propagated to the side irradiated with the ultraviolet light having the second wavelength. In this case, the photocatalytic activity of the photocatalyst supported on the side irradiated with the ultraviolet light having the second wavelength can also be enhanced by the ultraviolet light having the first wavelength. Further, the photocatalyst supported on the side irradiated with the ultraviolet light having the first wavelength may exhibit photocatalytic activity also by irradiation of the ultraviolet light having the second wavelength, and the ultraviolet light having the second wavelength may also be propagated to the side irradiated with the ultraviolet light having the first wavelength. In this case, the photocatalytic activity of the photocatalyst supported on the side irradiated with the ultraviolet light having the first wavelength can also be enhanced by the ultraviolet light having the second wavelength. In these cases, the ultraviolet light having the first wavelength and the ultraviolet light having the second wavelength can be used more effectively. Therefore, the bacteria and viruses collected on the photocatalyst supporting filter can be inactivated with higher probability.

Further, the ultraviolet light having the second wavelength may pass through the photocatalyst supporting filter. In this case, the collection filter can be irradiated with the ultraviolet light having the second wavelength. Therefore, an ability to inactivate the bacteria and viruses in the collection filter can be further improved in this case.

It is preferred that one wavelength out of the first wavelength and the second wavelength is 250 nm to 280 nm, and the other wavelength is 360 nm to 380 nm.

The ultraviolet light emitter for emitting ultraviolet light having a wavelength of 360 nm to 380 nm tends to emit ultraviolet light of higher intensity than the ultraviolet light emitter for emitting ultraviolet light having a wavelength of 250 nm to 280 nm. This tendency is particularly significant when the ultraviolet light emitter is constituted by LEDs (light emitting diodes). Therefore, by irradiating the photocatalyst supporting filter with the ultraviolet light having the wavelength of 360 nm to 380 nm which can be emitted from the ultraviolet light emitter with high intensity, the photocatalyst can exhibit high photocatalytic activity. On the other hand, the ultraviolet light having the wavelength of 250 nm to 280 nm has a higher ability to inactivate the bacteria and viruses than the ultraviolet light having the wavelength of 360 nm to 380 nm. Thus, the bacteria and viruses can be efficiently inactivated as a whole by a combination of the ultraviolet light for exhibiting high photocatalytic activity and the ultraviolet light having a high inactivation ability.

Further, it is preferred that the first wavelength be 250 nm to 280 nm, and the second wavelength be 360 nm to 380 nm.

The ultraviolet light having the first wavelength is ultraviolet light irradiated to the collection filter. As described above, since the ultraviolet light having the wavelength of 250 nm to 280 nm has a high ability to inactivate the bacteria and viruses, the bacteria and viruses attached to the dust collected on the collection filter can be more inactivated than when the first wavelength is 360 nm to 380 nm.

Further, in this case, it is preferred that the photocatalyst supporting filter supports the photocatalyst containing apatite on the side irradiated with the ultraviolet light having the first wavelength, and supports the photocatalyst containing titanium oxide on the side irradiated with the ultraviolet light having the second wavelength.

As described above, the ultraviolet light emitter for emitting the ultraviolet light having the wavelength of 360 nm to 380 nm tends to emit the ultraviolet light of higher intensity than the ultraviolet light emitters for emitting the ultraviolet light having the wavelength of 250 nm to 280 nm. Therefore, since the photocatalyst containing apatite having a high ability to adsorb and inactivate the bacteria and viruses is supported on the side irradiated with the ultraviolet light of a lower intensity first wavelength which is the wavelength of 250 nm to 280 nm, the bacteria and viruses can be more inactivated on the side irradiated with the ultraviolet light having the first wavelength of the photocatalyst supporting filter. In addition, since the photocatalyst containing titanium oxide is supported on the side irradiated with the ultraviolet light having a higher intensity second wavelength which is the wavelength of 360 nm to 380 nm, the bacteria and viruses can be more inactivated by an oxidizing ability of the titanium oxide. The photocatalyst containing apatite includes, for example, a titanium apatite, and the photocatalyst containing titanium oxide includes, for example, the titanium oxide itself.

Further, it is preferred that air flows from a side of the photocatalyst supporting filter to a side of the collection filter.

Generally, the micropores formed in the collection filter tend to be smaller than the micropores formed in the photocatalyst supporting filter. Thus, even the bacteria and viruses passing through the photocatalyst supporting filter can be collected by the collection filter. Thus, the bacteria and viruses can be distributed and collected by the collection filter and the photocatalyst supporting filter, as compared with the case where the air flows from the collection filter side to the photocatalyst supporting filter side. Therefore, the bacteria and viruses can be efficiently inactivated in each of the collection filter and the photocatalyst supporting filter, as compared with the case where the bacteria and viruses are biased and collected by the collection filter.

As described above, according to the present invention, there is provided the air cleaning apparatus capable of inactivating the bacteria and viruses collected on the collection filter and the photocatalyst supporting filter using the ultraviolet light, and efficiently using the ultraviolet light.

DESCRIPTION OF EMBODIMENTS

Hereinafter, preferred embodiments of an air cleaning apparatus according to the present invention will be described in detail with reference to the drawings.

First Embodiment

Figure 1:
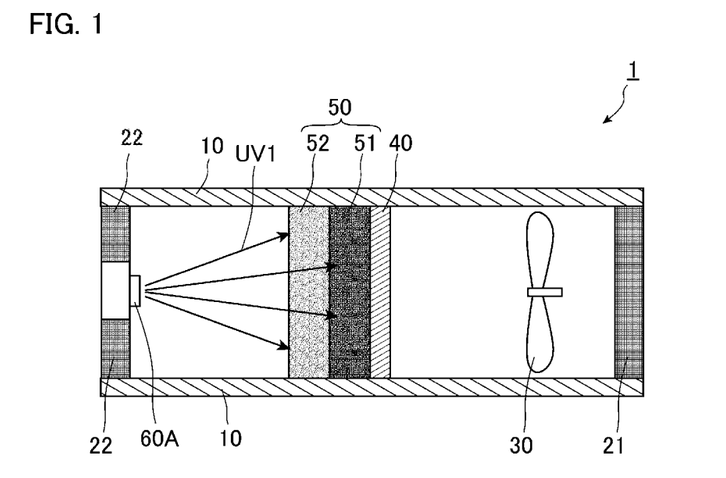
FIG. 1 is a cross-sectional view showing an air cleaning apparatus according to a first embodiment of the present invention.

FIG. 1 is a cross-sectional view showing an air cleaning apparatus according to the present embodiment. As shown in FIG. 1, an air cleaning apparatus 1 of the present embodiment includes a casing 10, an inlet coarse filter 21, an outlet coarse filter 22, a blower fan 30, a light shielding member 40, and a filter unit 50, and a first ultraviolet light emitter 60A as main components.

The casing 10 has a substantially cylindrical shape in this example. Note that ultraviolet light UV1 having a first wavelength may be irradiated to an inner wall surface of the casing 10 as described below. Therefore, it is preferred that the inner wall surface of the casing 10 be light reflective to reflect the ultraviolet light UV1 having the first wavelength.

One opening of the casing 10 is an air inlet, and the inlet coarse filter 21 is disposed at the air inlet. The other opening of the casing 10 is an air outlet, and the outlet coarse filter 22 is disposed at the air outlet. The inlet coarse filter 21 and the outlet coarse filter 22 are, for example, coarse dust filters capable of collecting at least a part of dust of a visible size, and formed with a large number of holes enough for passing the dust of a size difficult to visually recognize. Therefore, air resistance is small, and pressure loss at the air inlet and outlet is suppressed. Such a coarse filter includes, for example, a net-like filter made of resin or the like or a sponge-like filter.

The blower fan 30 receives power from a power supply (not shown), and rotates so that air flows from the inlet side to the outlet side. In FIG. 1, a propeller fan is shown as a fan constituting the blower fan 30, however, the blower fan 30 is not limited to the propeller fan but may be composed of another fan such as a sirocco fan.

The light shielding member 40 is disposed downstream of the blower fan 30 in air flow. The light shielding member 40 is configured not to block passage of air although it shields light. Such a light shielding member includes, for example, a member in which a pair of punching metal plates formed with a large number of openings is overlapped at a predetermined distance by shifting positions of openings, or a blind-like member in which a plurality of slats is arranged in parallel. Note that the light shielding member 40 may be irradiated with the ultraviolet light UV1 having the first wavelength as described below. Therefore, it is preferred that the light shielding member 40 be made of metal so that deterioration of a material constituting the light shielding member 40 does not occur, and a side irradiated with the ultraviolet light be light reflective to reflect the ultraviolet light UV1 having the first wavelength.

The filter unit 50 is disposed downstream of the light shielding member 40 in the air flow. The filter unit has a photocatalyst supporting filter 51 and a collection filter 52, and the photocatalyst supporting filter 51 is disposed upstream of the collection filter 52 in the air flow. The photocatalyst supporting filter 51 is a filter capable of collecting particles passing through the inlet coarse filter 21, and the collection filter 52 is a filter capable of collecting particles passing through the photocatalyst supporting filter 51. For example, the photocatalyst supporting filter 51 is a medium-performance filter having a collection rate of particles of 0.4 μm of less than 99%, and the collection filter 52 is a quasi-HEPA filter having a collection rate of particles of 0.3 μm of 90% or more.

The photocatalyst supporting filter 51 is a filter supporting a photocatalyst exhibiting photocatalytic activity by the ultraviolet light UV1 having the first wavelength. In the present embodiment, the first wavelength is 250 nm to 380 nm. Note that, in the present embodiment, when it is simply referred to as the ultraviolet light, it means the ultraviolet light UV1 having the first wavelength. Examples of the photocatalyst exhibiting photocatalytic activity by the ultraviolet light UV1 having the first wavelength includes a photocatalyst containing apatite and a photocatalyst containing titanium oxide. Examples of the photocatalyst containing apatite include titanium apatite in which titanium ions are introduced into apatite crystals such as calcium hydroxyapatite. Titanium apatite is preferable because it has an excellent ability to adsorb and inactivate bacteria and viruses. Further, examples of the photocatalyst containing titanium oxide include titanium oxide itself. The titanium oxide does not have as good adsorptivity as titanium apatite, but has an excellent ability to oxidize and inactivate adsorbed bacteria and viruses. Further, examples applicable to both the photocatalyst containing apatite and the photocatalyst containing titanium oxide include a hybrid photocatalyst of titanium oxide and apatite. The hybrid photocatalyst is a photocatalyst in which a plurality of apatite fine particles is immobilized on titanium oxide particles, and has both the excellent ability to adsorb the bacteria and viruses by apatite and the ability to inactivate the bacteria and viruses by titanium oxide. Hydroxyapatite or fluoroapatite may be immobilized on the titanium oxide particles. Further, other photocatalysts include tungsten oxide, zinc oxide and the like, however, at least one of the photocatalyst containing apatite and the photocatalyst containing titanium oxide is preferably supported from the viewpoint of having more excellent ability to inactivate the bacteria and viruses.

Filters used for the photocatalyst supporting filter 51 include a filter having a photocatalyst supported on a surface of fiber of nonwoven fabric. In order to support a particulate photocatalyst on the nonwoven fabric, non-cured binder in which the photocatalyst is dispersed is impregnated into the nonwoven fabric and then the photocatalyst may be immobilized on the surface of the nonwoven fabric by solidifying the binder. In this case, the binder may be inorganic or organic, and examples of the inorganic binder include silane compounds, and examples of the organic binder include acrylic compounds. Note that, the inorganic binder is preferable because it is suppressed from being decomposed by an oxidizing ability and the like of the photocatalyst as compared with the organic binder. Further, in order to support the particulate photocatalyst on the nonwoven fabric, a resin in which the particulate photocatalyst is dispersed may be spun to form the nonwoven fabric from resin fibers in which the photocatalyst is dispersed.

Or, the filters used for the photocatalyst supporting filter 51 include, for example, a filter which has wall members for dividing a large number of spaces in a honeycomb shape and contains particles of many photocatalysts enclosed in each space partitioned by the wall members. In this case, the particles of the photocatalyst are preferably granulated with the binder from the viewpoint of facilitating the air flow, and more preferably contain adsorptive particles such as activated carbon and zeolite in the granules from the viewpoint of improving deodorizing ability. Further, examples of the binder include the organic binder and the inorganic binder, and it is preferable to use the inorganic binder for the same reason as described above.

Further, the collection filter 52 is a filter for transmitting the ultraviolet light UV1 having the first wavelength. As described above, in the present embodiment, the first wavelength is 250 nm to 380 nm, and the collection filter 52 is made of a material for transmitting the ultraviolet light UV1 having the first wavelength. Specifically, the collection filter 52 is the nonwoven fabric made of resin fibers for transmitting the ultraviolet light UV1 having the first wavelength. Such resins include fluorine-based resins such as polytetrafluoroethylene and perfluoroalkoxyalkane, polypropylene, polyethylene and the like. Note that polypropylene and polyethylene are preferable because they are superior to the fluorine-based resins in adsorption of bacteria, viruses and the like. Further, it is preferred that the collection filter 52 transmits the ultraviolet light UV1 having the first wavelength through the resin constituting the filter, and transmits the ultraviolet light UV1 having the first wavelength also through micropores formed in the filter.

Further, in the present embodiment, the collection filter 52 is positively charged. The bacteria and viruses, or dust such as pollen are often negatively charged. Therefore, the collection filter 52 is positively charged, so that the collection rate of the dust, bacteria and viruses can be improved as compared with the case where the collection filter 52 is not charged. In order to positively charge the collection filter 52, for example, a high voltage of 5 kV to 30 kV may be applied to the nonwoven fabric made of resin fibers constituting the collection filter 52 for a predetermined time.

Further, in the present embodiment, the collection filter 52 is stacked in contact with the photocatalyst supporting filter 51. By the way, when the light is emitted from a light transmitting member, if a medium in contact with the member is the air, the light is less likely to propagate from the member to the air because a refractive index of the air is low. On the other hand, when the light transmitting member is in contact with another member, since the refractive index of the other member is higher than the refractive index of the air, the light easily propagates from the light transmitting member to the other member as compared to when the light transmitting member is in contact with the air. Therefore, at a portion where the resin constituting the collection filter 52 for transmitting the ultraviolet light UV1 having the first wavelength is in contact with the photocatalyst supporting filter 51, the ultraviolet light UV1 having the first wavelength easily propagates from the collection filter 52 to the photocatalyst supporting filter 51 as compared with a portion where the collection filter 52 is not in contact with the photocatalyst supporting filter 51. Therefore, when the ultraviolet light UV1 having the first wavelength is irradiated to the collection filter 52, the ultraviolet light UV1 having the first wavelength can be efficiently propagated to the collection filter 52 as compared to when the collection filter 52 is not in contact with the photocatalyst supporting filter 51.

In the filter unit 50, it is preferred that the photocatalyst supporting filter 51 and the collection filter 52 are integrated together, so that that the photocatalyst supporting filter 51 and the collection filter 52 can be simultaneously attached and detached from the casing 10 from the viewpoint of facilitating filter replacement.

The first ultraviolet light emitter 60A is a light emitter for emitting the ultraviolet light UV1 having the first wavelength which is a wavelength of 250 nm to 380 nm as described above. The first ultraviolet light emitter 60A irradiates the ultraviolet light UV1 having the first wavelength to the collection filter 52. The first ultraviolet light emitter 60A is made of, for example, a light emitter such as an LED or a black light. Note that since the LED has directionality in a light emission direction, it is preferable from the viewpoint of efficiently irradiating the collection filter 52 with the ultraviolet light UV1 having the first wavelength without irradiating light in useless directions.

In addition, if the first wavelength is 250 nm to 280 nm, it is easily absorbed by deoxyribonucleic acid (DNA) and ribonucleic acid (RNA), which is preferable from the viewpoint of having the excellent ability to inactivate the bacteria and viruses. On the other hand, if the first wavelength is 350 nm to 380 nm, it tends to emit higher intensity ultraviolet light from the first ultraviolet light emitter 60A, and it is preferable because it propagates the higher intensity ultraviolet light to the photocatalyst, so that the photocatalyst can exhibit higher photocatalytic activity. This tendency is higher when the LED is used as the first ultraviolet light emitter 60A.

Next, an operation of the air cleaning apparatus 1 configured as described above will be described.

When a power switch (not shown) is turned on, power is supplied from the power supply (not shown) to the blower fan 30 and the first ultraviolet light emitter 60A. When power is supplied, the blower fan 30 starts to rotate, and the first ultraviolet light emitter 60A emits the ultraviolet light UV1 having the first wavelength toward the collection filter 52.

At least a part of the ultraviolet light UV1 having the first wavelength emitted from the first ultraviolet light emitter 60A and irradiated to the collection filter 52 passes through the collection filter 52 and is irradiated to the photocatalyst supporting filter 51. As described above, since the photocatalyst supporting filter supports the photocatalyst exhibiting photocatalytic activity by the ultraviolet light UV1 having the first wavelength, the photocatalyst exhibits photocatalytic activity by irradiation of the ultraviolet light UV1 having the first wavelength.

In the present embodiment, since the collection filter 52 is made of the light transmitting material as described above, the ultraviolet light UV1 having the first wavelength passes through the resin constituting the collection filter 52, to pass through the collection filter 52. Therefore, in the present embodiment, the ultraviolet light UV1 having the first wavelength easily passes through the collection filter 52, so that the photocatalyst supporting filter 51 can be efficiently irradiated with the ultraviolet light UV1 having the first wavelength. Further, when the ultraviolet light UV1 having the first wavelength can pass also through the micropores of the collection filter 52, it is preferable because the ultraviolet light UV1 having the first wavelength can pass through the collection filter 52 more efficiently.

The dust may suppress transmission of the ultraviolet light UV1 having the first wavelength irradiated to a portion of the collection filter 52 to which the dust adheres. However, in the present embodiment, since the collection filter 52 is formed of the nonwoven fabric made of the light transmitting material as described above, the collection filter 52 can scatter the ultraviolet light. Therefore, the ultraviolet light UV1 having the first wavelength irradiated to a portion of the collection filter 52 to which the dust does not adhere so much is scattered during transmission, so that the ultraviolet light UV1 having the first wavelength can also be irradiated to a portion of the photocatalyst supporting filter 51 which is hard to be irradiated with the ultraviolet light UV1 having the first wavelength by the dust adhering to the collection filter 52. Therefore, the portion which is hard to be irradiated with the ultraviolet light UV1 having the first wavelength in the photocatalyst supporting filter 51 can be narrowed.

Further, in the present embodiment, as described above, the collection filter 52 made of the light transmitting material and the photocatalyst supporting filter 51 are stacked in contact with each other. Accordingly, in the portion where the collection filter 52 and the photocatalyst supporting filter 51 are in contact with each other, the ultraviolet light UV1 having the first wavelength is efficiently propagated from the collection filter 52 to the photocatalyst supporting filter 51. Therefore, the ultraviolet light UV1 having the first wavelength can be more efficiently irradiated to the photocatalyst supporting filter 51 than in the case where the collection filter 52 and the photocatalyst supporting filter 51 are separated from each other.

As described above, when the inner wall surface of the casing 10 reflects the ultraviolet light UV1 having the first wavelength, even if the ultraviolet light UV1 having the first wavelength propagates to the casing 10 due to any cause, it is reflected by the inner wall surface of the casing 10, and at least a portion of the reflected ultraviolet light UV1 having the first wavelength enters the collection filter 52. Therefore, the ultraviolet light UV1 having the first wavelength can be used efficiently.

A part of the ultraviolet light UV1 having the first wavelength propagated to the collection filter 52 may pass through the photocatalyst supporting filter 51 as well. In this case, if a side of the light shielding member 40 to be irradiated with the ultraviolet light is configured to reflect the ultraviolet light UV1 having the first wavelength as described above, the reflected ultraviolet light UV1 having the first wavelength can again enter the photocatalyst supporting filter 51. Therefore, the ultraviolet light UV1 having the first wavelength can be used efficiently.

In a state where the first ultraviolet light emitter 60A emits light, and the ultraviolet light UV1 having the first wavelength is irradiated to the photocatalyst supporting filter 51 as described above, the air flows into the casing 10 by rotation of the blower fan 30 via the inlet coarse filter 21 disposed at the inlet of the casing 10. The air flowing into the casing 10 passes through the light shielding member 40 and flows into the filter unit 50.

In the filter unit 50, since the photocatalyst supporting filter 51 is disposed upstream of the air flow as described above, the air flows into the photocatalyst supporting filter 51. The photocatalyst supporting filter collects at least a part of the dust, bacteria and viruses floating in the air. Further, the air passing through the photocatalyst supporting filter 51 flows into the collection filter 52. The collection filter 52 collects at least a part of the dust, bacteria, and viruses which are not collected by the photocatalyst supporting filter 51 and pass through the photocatalyst supporting filter 51.

At this time, in the present embodiment, since the collection filter 52 is positively charged as described above, the dust, bacteria, and viruses are collected at a high collection rate.

Since the collection filter 52 is irradiated with the ultraviolet light UV1 having the first wavelength as described above, the bacteria and viruses collected by the collection filter 52 are inactivated by the ultraviolet light. At this time, if the first wavelength is 250 nm to 280 nm as described above, it is preferable because the ability to inactivate the bacteria and viruses is high.

Further, the bacteria and viruses collected by the photocatalyst supporting filter 51 are oxidized and inactivated by the photocatalytic activity of the photocatalyst by the ultraviolet light UV1 having the first wavelength passing through the collection filter 52. Furthermore, even when the dust collected by the photocatalyst supporting filter 51 causes an offensive odor, the offensive odor can be suppressed by decomposing substances causing the offensive odor by the photocatalytic activity of the photocatalyst.

As described above, the air cleaning apparatus 1 of the present embodiment includes the collection filter 52 for collecting the dust, the first ultraviolet light emitter 60A for irradiating the collection filter 52 with the ultraviolet light UV1 having the first wavelength, and the photocatalyst supporting filter 51 which supports the photocatalyst exhibiting photocatalytic activity by the ultraviolet light UV1 having the first wavelength and collects the dust. The collection filter 52 transmits the ultraviolet light UV1 having the first wavelength, and the ultraviolet light UV1 having the first wavelength passing through the collection filter 52 is irradiated to the photocatalyst supporting filter 51.

According to such an air cleaning apparatus 1, the dust can be collected by the photocatalyst supporting filter 51 and the collection filter 52. Even when the bacteria and viruses are attached to the collected dust or when the bacteria and viruses are directly collected, since the collection filter 52 and the photocatalyst supporting filter 51 are irradiated with the ultraviolet light UV1 having the first wavelength emitted from the first ultraviolet light emitter 60A, the bacteria and viruses can be inactivated. Moreover, the ultraviolet light UV1 having the first wavelength irradiated to the photocatalyst supporting filter 51 is the ultraviolet light passing through the collection filter 52. Therefore, according to the air cleaning apparatus 1 of the present invention, it is possible to efficiently use the ultraviolet light emitted from the first ultraviolet light emitter 60A.

Further, in the present embodiment, the ultraviolet light is irradiated to the collection filter 52 charged positively. By irradiating the collection filter 52 with the ultraviolet light in this way, electrons of atoms or molecules constituting the collection filter 52 can be released. Therefore, even if positive charge of the collection filter 52 is reduced by receiving the electrons from the negatively charged dust, bacteria, viruses and the like, the positive charge of the collection filter 52 can be sustained for a longer period of time by irradiation of the ultraviolet light to the collection filter 52.

Second Embodiment

Next, a second embodiment of the present invention will be described in detail with reference to FIG. 2. Note that, the same or equivalent components as in the first embodiment are denoted by the same reference signs unless otherwise stated, and duplicate description will be omitted.

Figure 2:
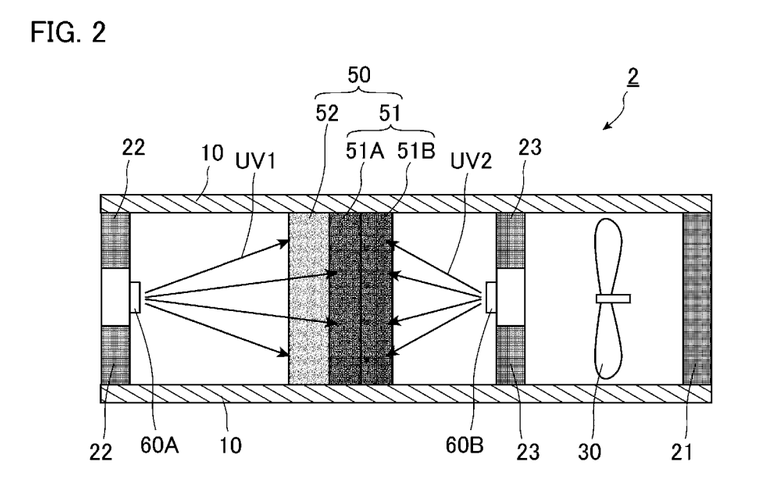
FIG. 2 is a cross-sectional view showing the air cleaning apparatus according to a second embodiment of the present invention.

FIG. 2 is a cross-sectional view showing the air cleaning apparatus according to the present embodiment. As shown in FIG. 2, an air cleaning apparatus 2 of the present embodiment is different from the air cleaning apparatus 1 of the first embodiment in that it does not include the light shielding member 40, but further includes an intermediate coarse filter 23 and a second ultraviolet light emitter 60B, and the photocatalyst supporting filter 51 includes a first photocatalyst supporting filter 51A and a second photocatalyst supporting filter 51B.

The intermediate coarse filter 23 is disposed between the blower fan 30 and the filter unit 50. The intermediate coarse filter 23 is a coarse dust filter capable of collecting at least a part of dust of a visible size, and formed with a large number of holes enough for passing the dust of a size difficult to visually recognize, similarly to the inlet coarse filter 21. Note that the intermediate coarse filter 23 may have a particle collection capacity similar to that of the inlet coarse filter 21, but is preferably a coarse dust filter formed with a hole smaller than the hole formed in the inlet coarse filter 21, and capable of collecting a visible dust passing through the inlet coarse filter 21.

The second ultraviolet light emitter 60B is a light emitter for emitting the ultraviolet light UV2 having a second wavelength different from the first wavelength toward the filter unit 50 from a side opposite to the first ultraviolet light emitter 60A. In the present embodiment, the first wavelength and the second wavelength are both in a range of 250 nm to 380 nm, and for example, the first wavelength is 250 nm to 280 nm, and the second wavelength is 360 nm to 380 nm.

The first photocatalyst supporting filter 51A constituting the photocatalyst supporting filter 51 is disposed on the collection filter 52 side, the second photocatalyst supporting filter 51B is disposed on the opposite side of the collection filter 52 side, and they are stacked in contact with each other. Therefore, the first photocatalyst supporting filter 51A is irradiated with the ultraviolet light UV1 having the first wavelength passing through the collection filter 52, and the second photocatalyst supporting filter 51B is irradiated with the ultraviolet light UV2 having the second wavelength emitted from the second ultraviolet light emitter 60B.

Therefore, the first photocatalyst supporting filter 51A supports the photocatalyst exhibiting photocatalytic activity by the ultraviolet light UV1 having the first wavelength, and the second photocatalyst supporting filter 51B supports the photocatalyst exhibiting photocatalytic activity by the ultraviolet light UV2 having the second wavelength. For example, when the first wavelength is 250 nm to 280 nm and the second wavelength is 360 nm to 380 nm as described above, the photocatalyst containing apatite is supported on the first photocatalyst supporting filter 51A, and the photocatalyst containing titanium oxide is supported on the second photocatalyst supporting filter 51B. Thus, it is preferred that the photocatalyst containing apatite having a high ability to adsorb and inactivate the bacteria and viruses is supported on a side irradiated with the ultraviolet light UV1 having a lower intensity first wavelength which is the wavelength of 250 nm to 280 nm, because the bacteria and viruses can be more inactivated on the side irradiated with the ultraviolet light UV1 having the first wavelength of the photocatalyst supporting filter.

Note that the photocatalyst supported on the first photocatalyst supporting filter 51A and the photocatalyst supported on the second photocatalyst supporting filter 51B may be the same type of photocatalyst. In this case, the photocatalyst exhibits photocatalytic activity even when irradiated with either the ultraviolet light UV1 having the first wavelength or the ultraviolet light UV2 having the second wavelength. For example, when the first wavelength is 250 nm to 280 nm and the second wavelength is 360 nm to 380 nm as described above, examples of the photocatalyst supported on both the first photocatalyst supporting filter 51A and the second photocatalyst supporting filter 51B include titanium oxide.

In such an air cleaning apparatus 2, when the switch (not shown) is turned on, the air flows from the inlet side to the outlet side by the rotation of the blower fan 30, and the ultraviolet light UV1 having the first wavelength is emitted from the first ultraviolet light emitter 60A, as in the air cleaning apparatus 1 of the first embodiment. Therefore, as in the air cleaning apparatus 1 of the first embodiment, the photocatalyst supported on the first photocatalyst supporting filter 51A exhibits photocatalytic activity by the ultraviolet light UV1 having the first wavelength passing through the collection filter 52 and irradiated to the first photocatalyst supporting filter 51A. Further, in the air cleaning apparatus 2 of the present embodiment, the ultraviolet light UV2 having the second wavelength is emitted from the second ultraviolet light emitter 60B when the switch is turned on. Therefore, the photocatalyst supported on the second photocatalyst supporting filter 51B also exhibits photocatalytic activity by the ultraviolet light UV2 having the second wavelength irradiated to the second photocatalyst supporting filter 51B.

Also in the present embodiment, as in the first embodiment, at least a part of the dust, bacteria and viruses is collected by the photocatalyst supporting filter 51 and the collection filter 52 in the air flow by the rotation of the blower fan 30. Then, the bacteria and viruses collected by the collection filter 52 are inactivated in the same manner as the air cleaning apparatus 1 of the first embodiment. Note that the first wavelength is preferably 250 nm to 280 nm because the ability to inactivate the bacteria and viruses is high. Further, the bacteria and viruses collected by the first photocatalyst supporting filter 51A out of the photocatalyst supporting filter 51 are oxidized and inactivated by the photocatalyst exhibiting photocatalytic activity by the ultraviolet light UV1 having the first wavelength. Furthermore, the bacteria and viruses collected by the second photocatalyst supporting filter 51B out of the photocatalyst supporting filter 51 are oxidized and inactivated by the photocatalyst exhibiting photocatalytic activity by the ultraviolet light UV2 having the second wavelength.

As described above, in addition to the air cleaning apparatus 1 of the first embodiment, the air cleaning apparatus 2 of the present embodiment further includes the second ultraviolet light emitter 60B for emitting the ultraviolet light UV2 having the second wavelength different from the first wavelength to a side opposite to the side of the photocatalyst supporting filter 51 irradiated with the ultraviolet light UV1 having the first wavelength. The photocatalyst supporting filter 51 supports the photocatalyst exhibiting a photocatalytic ability by irradiation of the ultraviolet light UV2 having the second wavelength on a side irradiated with the ultraviolet light UV2 having the second wavelength.

Thus, since the photocatalyst supporting filter 51 is irradiated with the ultraviolet light from both sides thereof, the photocatalyst can exhibit high photocatalytic activity on both the side irradiated with the ultraviolet light UV1 having the first wavelength and the side irradiated with the ultraviolet light UV2 having the second wavelength in the photocatalyst supporting filter 51. Therefore, the bacteria and viruses collected by the photocatalyst supporting filter 51 can be inactivated with higher probability. In addition, since the pieces of ultraviolet light of different wavelengths are irradiated to the photocatalyst supporting filter 51, it is possible to individually select a combination of the ultraviolet light UV1 having the first wavelength and the photocatalyst supported on the first photocatalyst supporting filter 51A, and a combination of the ultraviolet light UV2 having the second wavelength and the photocatalyst supported on the second photocatalyst supporting filter 51B. Therefore, according to the air cleaning apparatus 2 of the present embodiment, a degree of freedom in design can be improved.

In the present embodiment, it is also possible that the photocatalyst supported on the second photocatalyst supporting filter 51B exhibits photocatalytic activity even by irradiation of the ultraviolet light UV1 having the first wavelength, and the ultraviolet light UV1 having the first wavelength propagates to the second photocatalyst supporting filter 51B. In this case, the photocatalytic activity of the photocatalyst supported on the second photocatalyst supporting filter 51B can also be enhanced by the ultraviolet light UV1 having the first wavelength. In addition, it is also possible that the photocatalyst supported on the first photocatalyst supporting filter 51A exhibits photocatalytic activity even by irradiation with the ultraviolet light UV2 having the second wavelength, and the ultraviolet light UV1 having the first wavelength propagates to the second photocatalyst supporting filter 51B. In this case, the photocatalytic activity of the photocatalyst supported on the first photocatalyst supporting filter 51A can also be enhanced by the ultraviolet light UV2 having the second wavelength. Therefore, in these cases, the ultraviolet light UV1 having the first wavelength and the ultraviolet light UV2 having the second wavelength can be used more effectively, and the bacteria and viruses collected by the photocatalyst supporting filter 51 are inactivated with higher probability. In these cases, the photocatalyst supported on the first photocatalyst supporting filter 51A and the photocatalyst supported on the second photocatalyst supporting filter 51B may be the same type or different types.

Further, in the present embodiment, the ultraviolet light UV2 having the second wavelength may pass through the photocatalyst supporting filter 51. In this case, the collection filter 52 can be irradiated with the ultraviolet light UV2 having the second wavelength. In this case, the ability to inactivate the bacteria and viruses in the collection filter 52 can be further improved.

Further, as described in the first embodiment, the ultraviolet light emitter for emitting the ultraviolet light having the wavelength of 360 nm to 380 nm tends to emit the ultraviolet light of higher intensity than the ultraviolet light emitter for emitting the ultraviolet light having the wavelength of 250 nm to 280 nm. Therefore, by irradiating the photocatalyst supporting filter 51 with the ultraviolet light having the wavelength of 360 nm to 380 nm which can be emitted from the ultraviolet light emitter with high intensity, the photocatalyst can exhibit a high photocatalytic ability. Furthermore, as described in the first embodiment, the ultraviolet light having the wavelength of 250 nm to 280 nm has a higher ability to inactivate the bacteria and viruses than the ultraviolet light having the wavelength of 360 nm to 380 nm. Therefore, in the air cleaning apparatus 2 of the present embodiment, if one wavelength out of the first wavelength and the second wavelength is 250 nm to 280 nm and the other wavelength is 360 nm to 380 nm, the bacteria and viruses can be efficiently inactivated as a whole by a combination of the ultraviolet light for exhibiting high photocatalytic activity and the ultraviolet light having a high inactivation ability.

If the first wavelength is 250 nm to 280 nm and the second wavelength is 360 nm to 380 nm, the bacteria and viruses attached to the dust collected by the collection filter 52 can be more inactivated.

Although the present invention has been described above using the first and second embodiments as examples, the present invention is not limited thereto.

For example, unlike the above embodiments, the collection filter 52 may be a filter formed of a material such as a paper filter which is difficult to transmit the ultraviolet light UV1 having the first wavelength. In this case, although the collection filter 52 is preferably configured to transmit the ultraviolet light UV1 having the first wavelength from the micropores of the collection filter 52, for example, a window with a film for transmitting the ultraviolet light UV1 having the first wavelength may be provided in a portion of the collection filter 52. Further, the collection filter 52 may be formed of a fabric or the like in which fibers are regularly woven without being formed of the nonwoven fabric. Furthermore, the collection filter 52 may not be charged.

Further, unlike the above embodiments, the collection capacity of the photocatalyst supporting filter 51 and the collection capacity of the collection filter 52 may be approximately the same. Or, the photocatalyst supporting filter 51 may have a higher collection capacity than the collection filter 52. However, when the photocatalyst supporting filter 51 has a higher collection capacity than the collection filter 52, it is preferred that the air flow is in the opposite direction unlike the above embodiments.

Further, if a dust detection sensor is mounted, it is preferable because a time to replace the filter unit 50 can be known. Further, if an ultraviolet light detection sensor for detecting the ultraviolet light UV1 having the first wavelength is mounted between the collection filter and the photocatalyst supporting filter 51, it is possible to detect that the dust accumulates in the collection filter 52 and the ultraviolet light UV1 having the first wavelength is difficult to be transmitted, and it is preferable because the time to replace the filter unit 50 can be known.

Further, in the above embodiments, although the photocatalyst supporting filter 51 and the collection filter 52 are stacked in contact with each other, the photocatalyst supporting filter 51 and the collection filter 52 may be separated from each other. Further, the first photocatalyst supporting filter 51A and the second photocatalyst supporting filter 51B in the second embodiment may be stacked in a state separated from each other. Further, in the filter unit 50, the photocatalyst supporting filter 51 and the collection filter 52 may be removed individually, or the first photocatalyst supporting filter 51A and the second photocatalyst supporting filter 51B may be removed separately.

As described above, according to the present invention, it is possible to provide the air cleaning apparatus capable of inactivating the bacteria and viruses collected by the filter and the photocatalyst supporting filter using the ultraviolet light, and efficiently using the ultraviolet light, and the air cleaning apparatus can be used in fields such as a household air cleaning apparatus, a large scale air cleaning apparatus in factories or the like.

REFERENCE SIGNS LIST 1, 2 . . . air cleaning apparatus
10 . . . casing

30 . . . blower fan
40 . . . light shielding member
50 . . . filter unit
51 . . . photocatalyst supporting filter
51A . . . first photocatalyst supporting filter
51B . . . second photocatalyst supporting filter
52 . . . collection filter
60A . . . first ultraviolet light emitter
60B . . . second ultraviolet light emitter
UV1 . . . ultraviolet light having first wavelength
UV2 . . . ultraviolet light having second wavelength.

The invention claimed is:

1. An air cleaning apparatus comprising:
a collection filter that collects dust;
a first ultraviolet light emitter that irradiates the collection filter with ultraviolet light having a first wavelength;
a photocatalyst supporting filter that supports a photocatalyst exhibiting photocatalytic activity by the ultraviolet light having the first wavelength and collects the dust; and
a second ultraviolet light emitter that irradiates ultraviolet light having a second wavelength different from the first wavelength to a side opposite to a side of the photocatalyst supporting filter irradiated with the ultraviolet light having the first wavelength,
wherein the photocatalyst supporting filter supports the photocatalyst exhibiting photocatalytic activity by the ultraviolet light having the first wavelength on the side irradiated with the ultraviolet light having the first wavelength, and supports the photocatalyst exhibiting photocatalytic activity by the ultraviolet light having the second wavelength on the side irradiated with the ultraviolet light having the second wavelength,
wherein the collection filter transmits the ultraviolet light having the first wavelength,
wherein the ultraviolet light having the first wavelength passing through the collection filter is irradiated to the photocatalyst supporting filter, and
wherein the first wavelength is 250 nm to 280 nm, and the second wavelength is 360 nm to 380 nm.

2. The air cleaning apparatus according to claim 1, wherein the collection filter is made of a light transmitting material.

3. The air cleaning apparatus according to claim 2, wherein the collection filter is made of a nonwoven fabric.

4. The air cleaning apparatus according to claim 2, wherein the collection filter and the photocatalyst supporting filter are stacked in contact with each other.

5. The air cleaning apparatus according to claim 1, wherein the collection filter is positively charged.

6. The air cleaning apparatus according to claim 1, wherein the photocatalyst supporting filter supports the photocatalyst containing apatite on the side irradiated with the ultraviolet light having the first wavelength, and supports the photocatalyst containing titanium oxide on the side irradiated with the ultraviolet light having the second wavelength.

7. The air cleaning apparatus according to claim 1, wherein air flows from a side of the photocatalyst supporting filter to a side of the collection filter.

* * * * *